(12) United States Patent
Spence

(10) Patent No.: US 10,709,597 B2
(45) Date of Patent: Jul. 14, 2020

(54) ROBOTIC RADIAL ARM BOARD FOR USING IN CARDIAC PROCEDURES

(71) Applicant: Patrick H. Spence, Aldan, PA (US)

(72) Inventor: Patrick H. Spence, Aldan, PA (US)

(*) Notice: Subject to any disclaimer, the term of this patent is extended or adjusted under 35 U.S.C. 154(b) by 392 days.

(21) Appl. No.: 15/476,389

(22) Filed: Mar. 31, 2017

(65) Prior Publication Data

US 2017/0281395 A1 Oct. 5, 2017

Related U.S. Application Data

(60) Provisional application No. 62/316,821, filed on Apr. 1, 2016.

(51) Int. Cl.
*A61G 13/12* (2006.01)
*A61F 5/37* (2006.01)

(52) U.S. Cl.
CPC .................. *A61F 5/3761* (2013.01)

(58) Field of Classification Search
CPC ........ A61F 5/37; A61F 5/3761; A61F 5/3769; A61G 7/075; A61G 7/1092; A61G 13/0036; A61G 13/0045; A61G 13/0072; A61G 13/02; A61G 13/04; A61G 13/06; A61G 13/08; A61G 13/12; A61G 13/1205; A61G 13/1235; A61G 13/124; A61G 13/1245; A61G 13/1255; A61G 13/129; A61G 13/1295; A61G 15/02; A61G 15/12; A61G 2210/50; A61M 5/52; A61B 6/0457; B25J 9/042
USPC .... 5/601, 621, 623; 128/845, 877, 878, 879; 248/118; 600/415
See application file for complete search history.

(56) References Cited

U.S. PATENT DOCUMENTS

| | | | | |
|---|---|---|---|---|
| 2,237,252 A | * | 4/1941 | Longfellow | A61G 7/075 602/20 |
| 2,972,505 A | * | 2/1961 | Weickgenannt | A61G 13/12 5/646 |
| 4,669,451 A | * | 6/1987 | Blauth | A61F 5/013 482/901 |
| 5,027,799 A | | 7/1991 | Laico et al. | |
| 5,135,210 A | * | 8/1992 | Michelson | A61G 13/12 5/623 |
| 5,184,601 A | | 2/1993 | Putman | |
| 5,291,903 A | | 3/1994 | Reeves | |
| 5,586,163 A | | 12/1996 | Goldstein | |
| 5,940,912 A | * | 8/1999 | Keselman | A61G 13/1235 297/411.35 |
| 7,222,826 B1 | | 5/2007 | Berglund | |
| 9,636,268 B1 | * | 5/2017 | Bedillion | A61G 13/1235 |
| 10,130,542 B1 | * | 11/2018 | Strawder | A61G 13/121 |

(Continued)

*Primary Examiner* — Anna K Kinsaul
*Assistant Examiner* — Camtu T Nguyen
(74) *Attorney, Agent, or Firm* — Dunlap, Bennett & Ludwig, PLLC

(57) ABSTRACT

Embodiments of the present invention include a radial arm board for use during a cardiac procedure with an upper arm board and a lower arm board. The radial arm board includes one or more motors to control the position of the arm with a control panel. The components of the radial arm board can be moved laterally, raised, and lowered, thus allowing multiple degrees of freedom for the device. The radial arm allows comfort for the patient, accessibility of the arm to the doctor, and eliminates the need for manual manipulation of the radial arm board.

7 Claims, 3 Drawing Sheets

(56) References Cited

U.S. PATENT DOCUMENTS

| | | |
|---|---|---|
| 2003/0028967 A1 | 2/2003 | Schuerch |
| 2005/0052066 A1 | 3/2005 | Wright |
| 2012/0255122 A1* | 10/2012 | Diel .................. A61G 13/0036 |
| | | 5/610 |
| 2014/0059772 A1 | 3/2014 | Crisco et al. |
| 2014/0221811 A1 | 8/2014 | Sampognaro |
| 2015/0335831 A1* | 11/2015 | De Zayas ............... A61M 5/52 |
| | | 128/877 |
| 2016/0242981 A1* | 8/2016 | Debatty ............... A61B 6/0407 |

* cited by examiner

ROBOTIC RADIAL ARM BOARD FOR USING IN CARDIAC PROCEDURES

CROSS-REFERENCE TO RELATED APPLICATION

This application claims the benefit of priority of U.S. provisional application No. 62/316,821 filed on Apr. 1, 2016, the contents of which are herein incorporated by reference.

BACKGROUND OF THE INVENTION

The present invention relates to radial arm boards, and more particularly to a robotically controlled, radial arm board for use during cardiac procedure.

Coronary diseases remain a leading cause of morbidity and mortality in Western societies and are treated using several approaches. R is often sufficient to treat the symptoms with pharmaceuticals and lifestyle modification to lessen the underlying causes of the disease. In more severe cases, however, it may be necessary to treat the coronary disease using interventional medical procedures such as cardiac catheterization.

Current radial boards are maneuvered into position manually and generally move only on a single axis. They are not comfortable for the patient and do not allow movement suitable to the normal hand. Additionally, the doctor or assistant must struggle with manually finding a position that is both comfortable for the patient and allows access to the necessary veins or arteries. Further, the board include gel pads to raise the patient's hand and tape the patient's hand for stability. This is often uncomfortable for the patient.

Thus, there exists a need for a more comfortable radial board that allows for more degrees of freedom in movement, comfort for the patient, and easier control by the physician or assistant.

SUMMARY

In one embodiment, a radial arm board for use during a cardiac procedure includes a planar upper arm board to stabilize a patient's upper arm where a proximal end of the planar upper arm board is coupled to a clip. The radial arm further includes a planar lower arm board to stabilize a patient's lower arm, wherein the planar lower arm board is coupled to a distal end of the planar upper arm board. Further included is at least one motor operable to move the planar upper arm board with respect to the clip, and the planar lower arm board with respect to the upper arm.

In one embodiment, the planar upper arm board comprises an upper clip, within which the lower planar arm board is positioned. In one embodiment, the arm board further comprised at least two sprockets, the sprockets comprising interlocking teeth, and the sprockets being rotated by an interlocking shaft.

In one embodiment, the planar upper arm board moves at an angle of up to 180 degrees with respect to a horizontal axis created by the clip. In one embodiment, the planar upper arm board moves in a clockwise or counterclockwise movement.

In one embodiment, the planar lower arm board moves up to 45 degrees with respect to a horizontal axis created by an upper clip of the planar upper arm board.

In one embodiment, the planar upper arm board is raised or lowered by controlling the motor. In one embodiment, the planar lower arm board moves in a clockwise or counterclockwise direction with respect to a horizontal axis created by an upper arm clip of the planar upper arm board.

In one embodiment, the arm board includes a remote control to control the motor. The arm board can include a locking mechanism to lock the planar upper arm board and planar lower arm board in place.

In one embodiment, the planar upper arm board further comprises an upper adjustable arm strap to hold the patient's arm in place. In one embodiment, the planar lower arm board further comprises a lower adjustable arm strap to hold the patient's lower arm in place. In one embodiment, the arm board includes a tray to which the clip is attached, and the tray is attached to an operating table.

DETAILED DESCRIPTION OF THE INVENTION

A description of preferred embodiments of the invention follows. Current radial arm boards do not provide a range of movement and can generally only be moved on one axis. Additionally, they require manually maneuvering the board without any automated control.

The current invention is a robotic radial arm board that can be moved laterally (with respect to an X and Y axis) and vertically (raised and lowered along a Z axis.) Advantageously, it can be locked into place. The board offers comfort and increased mobility of the arm. Further, the position of the board includes a motor component, such that the board can be controlled without manual manipulation and via an external control panel.

Figure 1:
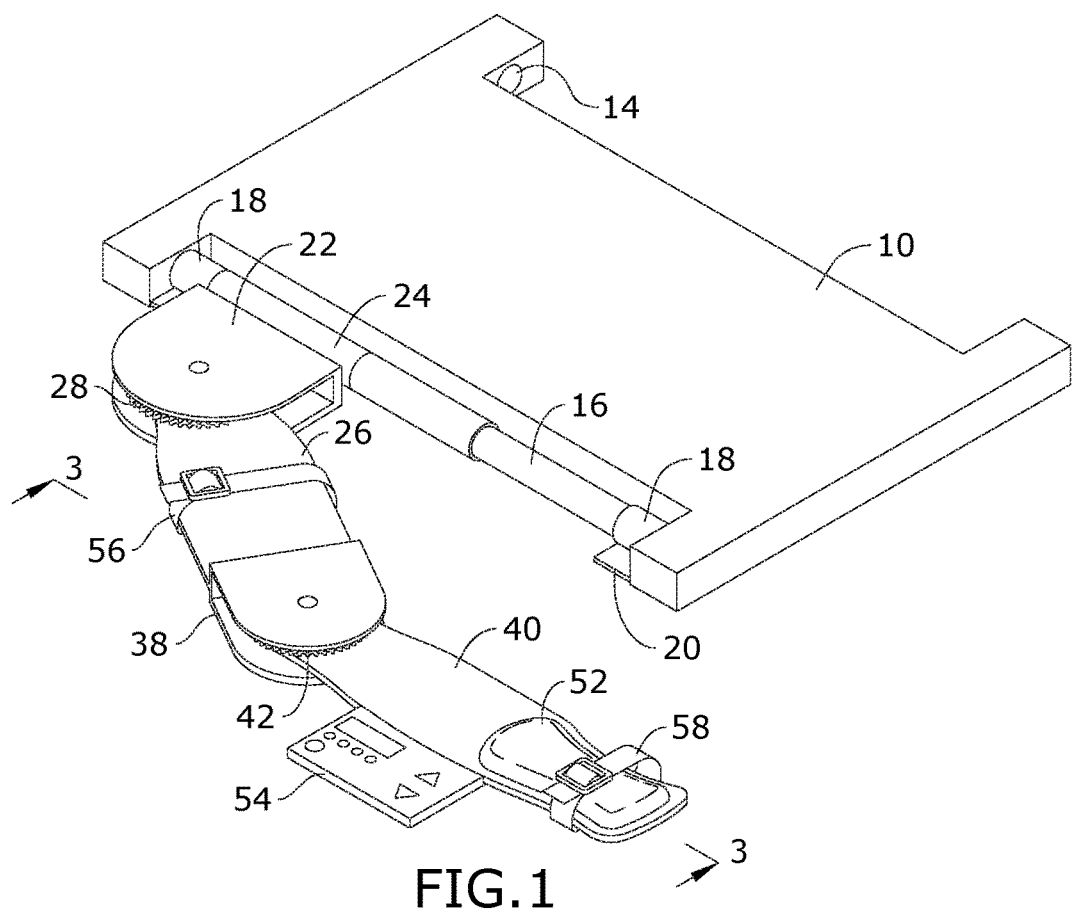
FIG. 1 is a perspective view of a radial arm board, shown in a right arm support position.
Figure 2:
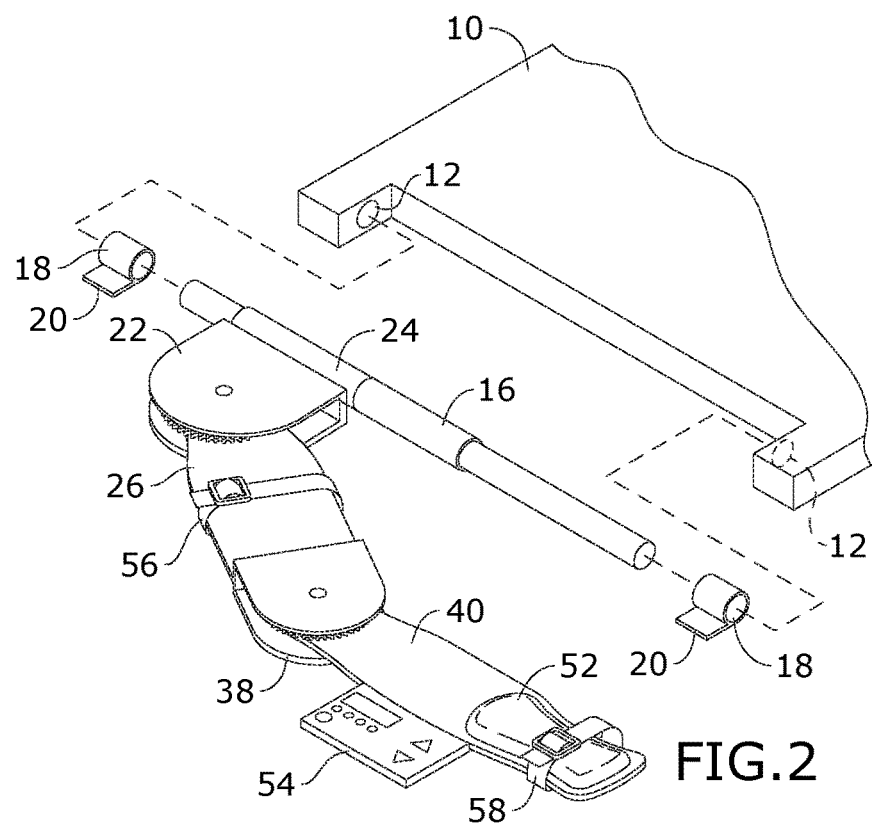
FIG. 2 is partial exploded view of the radial arm board; it being understood that FIG. 2 illustrates two embodiments of motors simultaneously: one embodiment, a motor 34 holds an upper arm small sprocket 30, wherein the motor 34 acts as a rotating shaft to rotate the sprocket 30, and a small sprocket 30 and a large sprocket 28 comprise interlocking teeth, and thus both sprockets 30 and 28 rotate due to motor 34; and a second embodiment of a potential motor, wherein the motor 34 engages a pulley 36 so that the motor 34 rotates and the pulley 36 rotates. It is also understood that the present invention can work as disclosed herein when only one of the two embodiments of motors are present.

In the embodiment of FIGS. 1 and 2, a radial arm board includes a tray 10 that can be coupled to an operating table using a hinge or any suitable means. Alternatively, the tray 10 can simply be stored under the operating table. The tray 10 is substantially planar and includes a right pin holes 12 and a left sided pin holes 14. The tray further includes a pin 16. A proximal and a distal end of the pin 16 are positioned in the pin holes 12. A proximal and distal end of a second pin 16 can be positioned in pin holes 14. The pin 16 includes a sleeve 18 at the proximal and distal end of the pin 16. The tray 10 also includes a pin sleeve tab 20 coupled to each pin 16.

In one embodiment, the tray 10 can fit under a pad on the operating table, and the patient lays on top of the pad. In one embodiment, the tray 10 has electric panels for a lithium battery to power the radial arm. The pin 16 acts as the motorized shaft on the side of the tray 10. The tray 10 can therefore have two motorized shafts; pins 16 on the left and ride side of the tray 10.

The radial arm board includes a clip 22 and a clip sleeve 24. Further included is an upper arm board 26 to hold an upper arm of a patient. The upper arm board 26 is positioned within the clip 22. An upper arm sprocket 28 is also within the clip 22 and can engage and allow movement of the upper arm board 26. The upper arm board 26 can include an adjustable strap 56 for holding a patient's upper arm in place. The upper arm board 26 can further include an upper arm clip 38. The upper arm portion 26 is substantially planar.

In one embodiment, the clip 22 can slide onto the pin 16. The upper arm board 26 is attached to the clip 22. The pin 16 can includes a push button that opens a groove within the clip sleeve 24, within which a component of the clip 22 fits. The groove secures the clip 22, but allows up and down movement of the clip 22. In one embodiment, the clip sleeve 24 includes a five-piece groove chain spindle so the clip 22 will not come off a track on the pin 16. The push button can be operated manually or with a control panel 54. A locking mechanism is further included on the clip 22 to lock the upper arm board 26 into place, either manually or with control panel 54.

The radial arm can include a lower arm board 40, which is substantially planar. The lower arm board 40 is in communication with the upper arm board 26. Upper arm board 26 further includes an upper arm clip 38, within which the lower arm board 40 is positioned. The upper arm clip 38 includes a lower arm sprocket 42, which engages the lower arm board 40. The lower arm board 40 can include an adjustment strap 58 to hold the patients lower arm in place. The lower arm board 40 can further include a pad 52 for additional comfort for a patient's lower arm. The pad 52 can be made of foam, fabric, or any suitable soft material.

The lower arm board 40 can also include a removable control panel 54 for a controller (a physician or assistant) to maneuver or control the position of the radial board with at least one motor. It is to be understood, however, that the removable control panel 54 can be placed or used anywhere on or outside of the device.

Figure 3:
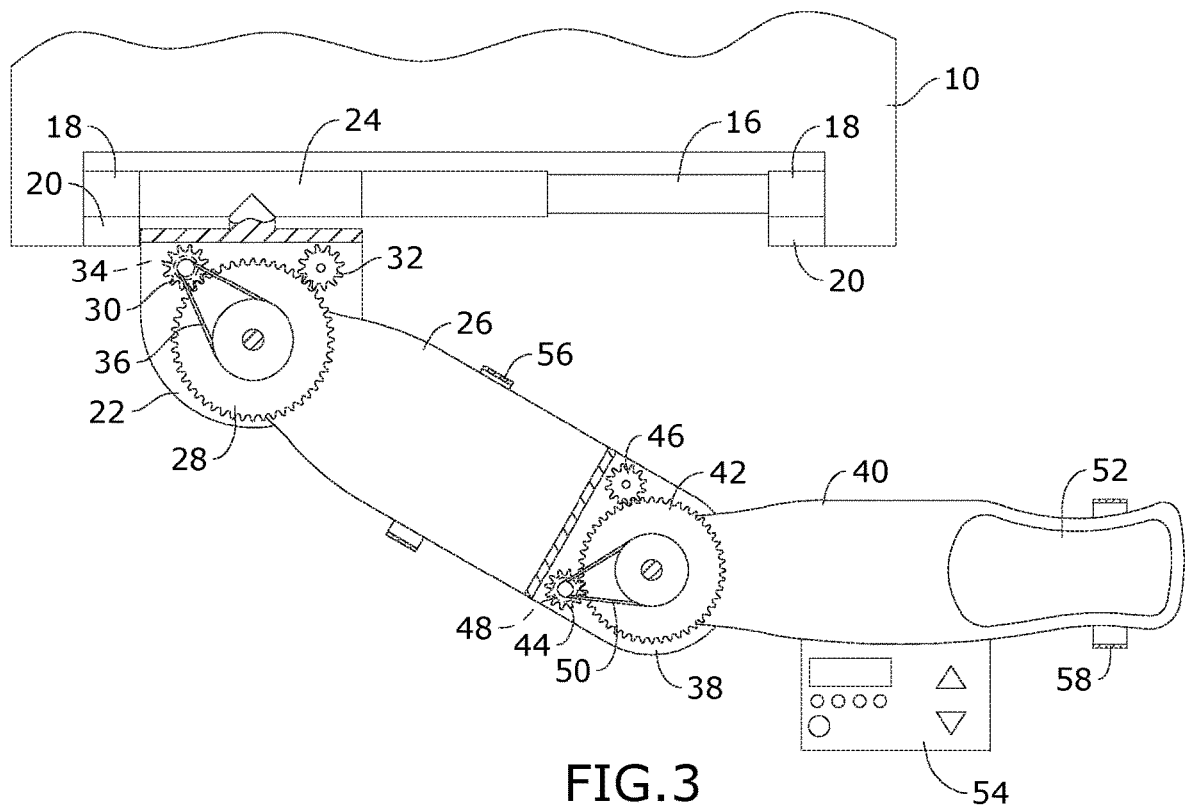
FIG. 3 is a section view of the radial arm board taken along line 3-3 of FIG. 1.

FIG. 3 shows a section view, taken along line 3-3 in FIG. 1. Two embodiments of two potential motors are shown. In one embodiment, a motor 34 holds an upper arm small sprocket 30. The motor 34 acts as a rotating shaft to rotate the sprocket 30. The small sprocket 30 and a large sprocket 28 comprise interlocking teeth, and thus both sprockets 30 and 28 rotate due to motor 34.

In a second embodiment of a potential motor, the motor 34 engages a pulley 36. As the motor 34 rotates, the pulley 36 rotates.

The lower arm board 40 includes a lower arm motor 48. Like the upper arm board 26, two embodiments of two motors are shown. A rotatable motor 48 acts to rotate a lower arm small sprocket 44. The lower arm small sprocket 44 and the lower arm large sprocket 42 comprise interlocking teeth, and thus both sprockets 44 and 42 rotate due to motor 48.

Alternatively, motor 48 can engage a lower arm pulley 50. As the motor 48 rotates, the pulley 50 rotates. In an alternative embodiment, optional upper arm small sprocket 32 and lower arm small sprocket 46 show that the motors can be positioned on either side of the clips 22 and 38.

In one embodiment, upper motor 34 and lower motor 48 can be controlled by the removable control panel 54. Advantageously, manual manipulation of the radial board is not needed.

Figure 4:
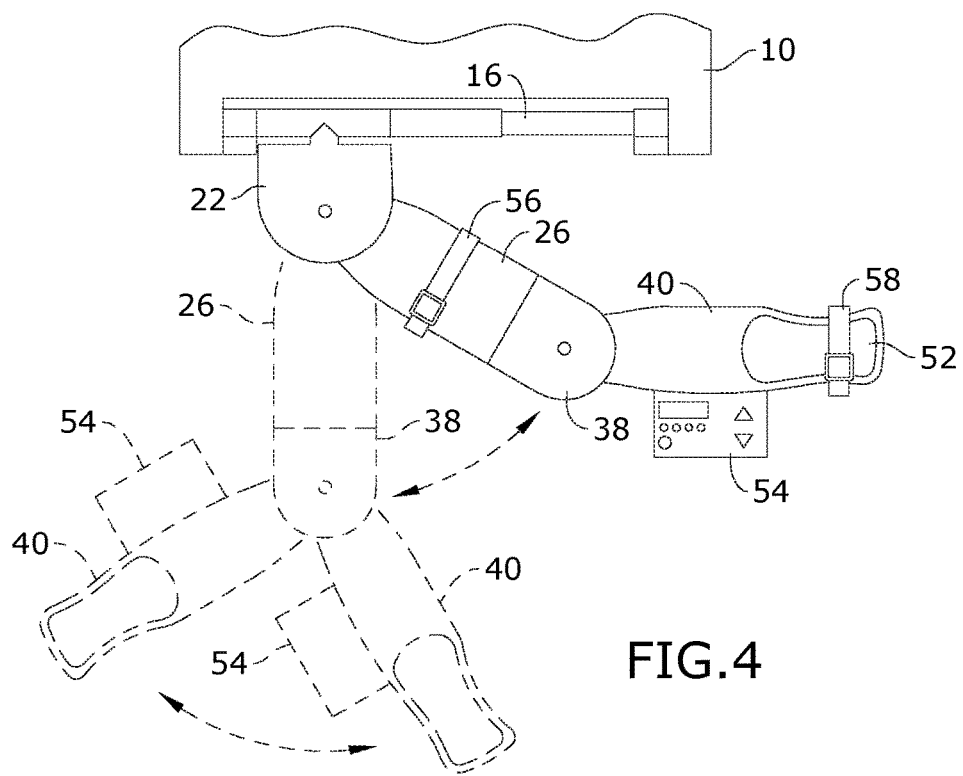
FIG. 4 is a top view of a radial arm board.

The embodiment of FIG. 4 shows a top view of the radial arm. Upper arm board 26 can rotate up to a 180-degree angle with respect to a horizontal axis created by the clip 22. The upper arm board 26 can move in a clockwise or counter-clockwise direction. Lower arm board 40 can rotate up to a 45 angle clockwise or counterclockwise with respect to a horizontal axis created by the clip 38, thus allowing it about a 90-degree range of movement. Advantageously, this allows the controller to position the patient's arm to a comfortable as well as accessible position for a procedure to be completed. The components of the radial arm board may be prepared using any suitable materials.

Figure 5:
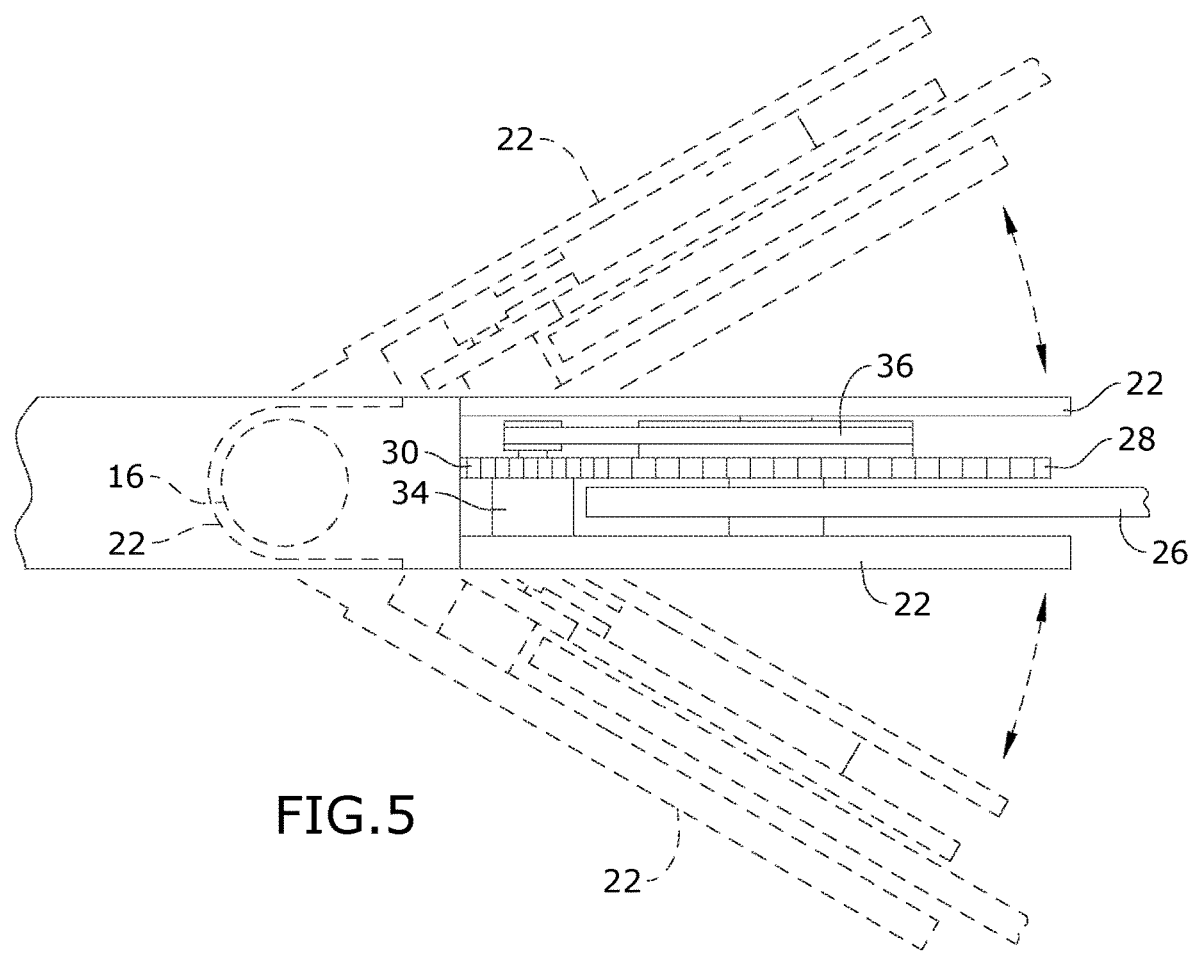
FIG. 5 is a side view of a radial arm board.

The embodiment of FIG. 5 shows a side view of the radial board with components between clip 22. In one embodiment, the clip 22 with upper arm board 26 of the radial arm can be raised or lowered from a 0-degree angle to about a 45 degree angle up or down with respect to a horizontal axis created by pin 16, thus raising or lowering the entire radial arm. The upper arm 26 rotates up or down on the pin 16, which acts as a motorized shaft. The up and down angular movement can be controlled with control panel 54 with motors coupled to the radial arm.

It is to be understood that the angles that the components of the radial arm are moved laterally, or the angle at which the radial arm is raised or lowered can be adjusted to be greater or less than those described.

Figure 6:
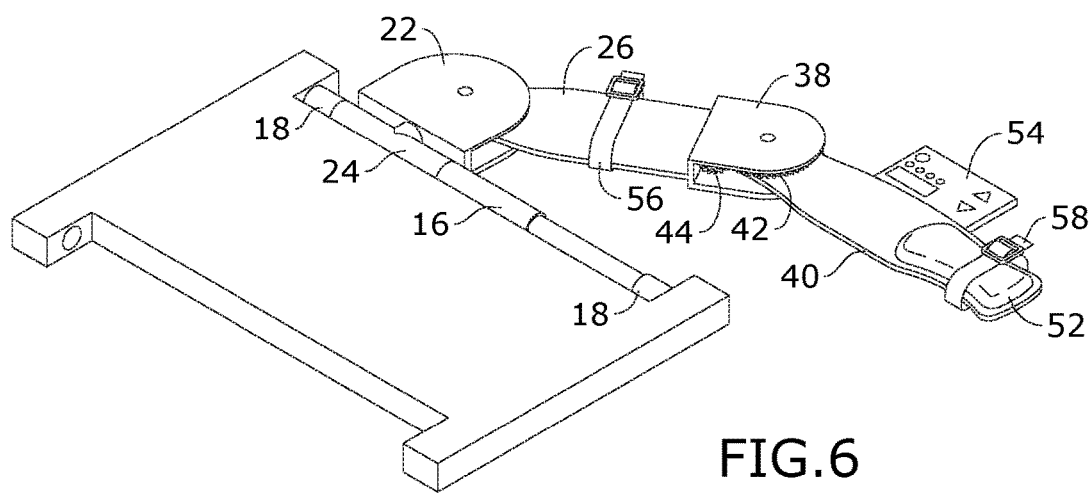
FIG. 6 is a perspective view of a radial arm board, shown in a left arm support position.

The embodiment of FIG. 6 shows a radial board in a left arm support position. The components are all the same as for the previously described right sided radial board. In one embodiment, the clip 22 can be released from the right sided pin 16 by the push button on the clip 22 to open the groove on clip sleeve 24. The clip 22 can be turned and then attached the left sided pin 16 on the tray 10 for left sided use just as it was attached to the right side. The position can be controlled with the control panel 54 as previously described, and locked into place with the locking mechanism.

It is to be understood that though motors 34 and 48 are described to allow control of the radial board position, any suitable motors can be used. Motors can include alternating Current (AC) motors, direct-current (DC) motors, servo motors, or step motors. In an alternative embodiment, the radial board can be controlled through a mobile or computerized application. The motors of the radial board can be battery operated, or powered by alternative powering means. Advantageously, if the motors or other powering sources fail, the radial arm can still be maneuvered manually.

In another embodiment, a method is provided for conducting a cardiac procedure on a patient. The method comprises supporting the arm of the patient lying in a supine position on an operating table. The radial board is coupled to and extends from the operating table. The patient places an arm on the radial board. Adjustment straps 58 and 26 can be used to hold the patients' upper and lower arm in place. The position of the radial board can be adjusted using the remote 54 by the physician or other controller such that the patient is comfortable and the physician has access to the needed arteries for the procedure.

It should be understood, of course, that the foregoing relates to exemplary embodiments of the invention and that modifications may be made without departing from the spirit and scope of the invention as set forth in the following claims.

What is claimed is:

1. An arm board for use along either side of an operating table, comprising:
 a planar upper arm board to stabilize a patient's upper arm, a proximal end of the upper arm board coupled to a clip;
 a planar lower arm board to stabilize a patient's lower arm, wherein the planar lower arm board is in communication with a distal end of the planar upper arm board;
 an upper motor operable to move the planar upper arm board with respect to the clip;
 a lower motor operable to move the planar lower arm board with respect to the upper arm;
 a tray having a left end and a right end on opposing ends thereof;
 the left and right ends each providing a pair of opposing left and right holes respectively;
 a first motorized pin shaft adapted to operatively associate with the clip; and
 the first motorized pin dimensioned to operably associate with either pair of opposing left and right holes,
 a control panel to control the upper motor, the lower motor, and the first motorized shaft,
 whereby the tray is adapted to lay under a patient so that without moving said tray, the first motorized shaft can be moved between the pair of opposing left and right holes, thereby not disturbing the patient while treating both left and right arms of the patient.

2. The arm board of claim 1, wherein the planar upper arm board further comprises an upper adjustable arm strap to hold the patient's upper arm in place.

3. The arm board of claim 1, wherein the planar upper arm board comprises an upper clip, within which the lower planar arm board is positioned.

4. The arm board of claim 1, wherein the planar lower arm board further comprises a lower adjustable arm strap to hold the patient's lower arm in place.

5. The arm board of claim 1, wherein the planar upper arm board moves at an angle of up to 180 degrees about a pivot point provided by the clip.

6. The arm board of claim 1, wherein the planar upper arm board moves in a clockwise or counterclockwise movement.

7. The arm board of claim 1, wherein the planar lower arm board can move up to 45 degrees in a clockwise or counterclockwise direction about a pivot point provided by an upper clip of the planar upper arm board.

* * * * *